United States Patent

Lippsmeier et al.

[11] 4,080,384
[45] Mar. 21, 1978

[54] PRODUCTION OF (HYDROXYMETHYL)-ALKYL, CYCLOALKYL AND ARALKYLPHOSPHINES

[75] Inventors: Bernd Lippsmeier, Hurth-Knapsack; Klaus Hestermann, Erftstadt Bliesheim; Gero Heymer, Erftstadt Liblar, all of Germany

[73] Assignee: Hoechst Aktiengesellschaft, Frankfurt am Main, Germany

[21] Appl. No.: 559,529

[22] Filed: Mar. 18, 1975

[30] Foreign Application Priority Data

Mar. 22, 1974   Germany .......................... 2413825

[51] Int. Cl.$^2$ .............................................. C07F 9/50
[52] U.S. Cl. .............................................. 260/606.5 P
[58] Field of Search ................................. 260/606.5 P

[56] References Cited

U.S. PATENT DOCUMENTS

| | | | |
|---|---|---|---|
| 2,916,346 | 12/1959 | Jalkanen .......................... | 23/283 X |
| 2,999,882 | 9/1961 | Buckler et al. ................. | 260/606.5 P |
| 3,030,421 | 4/1962 | Reuter et al. .................. | 260/606.5 P |
| 3,145,227 | 8/1964 | Grayson et al. ................ | 260/606.5 P |
| 3,243,450 | 3/1966 | Grayson ......................... | 260/606.5 P |
| 3,267,149 | 8/1966 | Garner ........................... | 260/606.5 P |
| 3,660,495 | 5/1972 | Chingtsung Lin ............. | 260/606.5 P |
| 3,704,325 | 11/1972 | Stockel ........................... | 260/606.5 P |
| 3,729,516 | 4/1973 | Stockel ........................... | 260/606.5 P |

OTHER PUBLICATIONS

Hellmann et al., Ann. V659, pp. 49–63 (1962).

*Primary Examiner*—Helen M. S. Sneed
*Attorney, Agent, or Firm*—Connolly and Hutz

[57] ABSTRACT

Production of (hydroxymethyl)-alkyl, cycloalkyl or aralkylphosphines of the general formula:

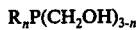

$$R_nP(CH_2OH)_{3-n}$$

in which $n$ stands for 1 or 2 and R stands for identical or different, substituted or unsubstituted alkyl, cycloalkyl or aralkyl radicals having from 1 to 18 carbon atoms. The compounds are made by reacting suitable mono- or di-alkyl, cycloalkyl or aralkylphosphines at atmospheric pressure and at temperatures lower than 40° C with formaldehyde, paraformaldehyde or trioxane in the presence of polar organic solvents being inert with respect to the resulting reaction product, and separating the solvent from the reaction product.

4 Claims, 1 Drawing Figure

U.S. Patent  March 21, 1978  4,080,384
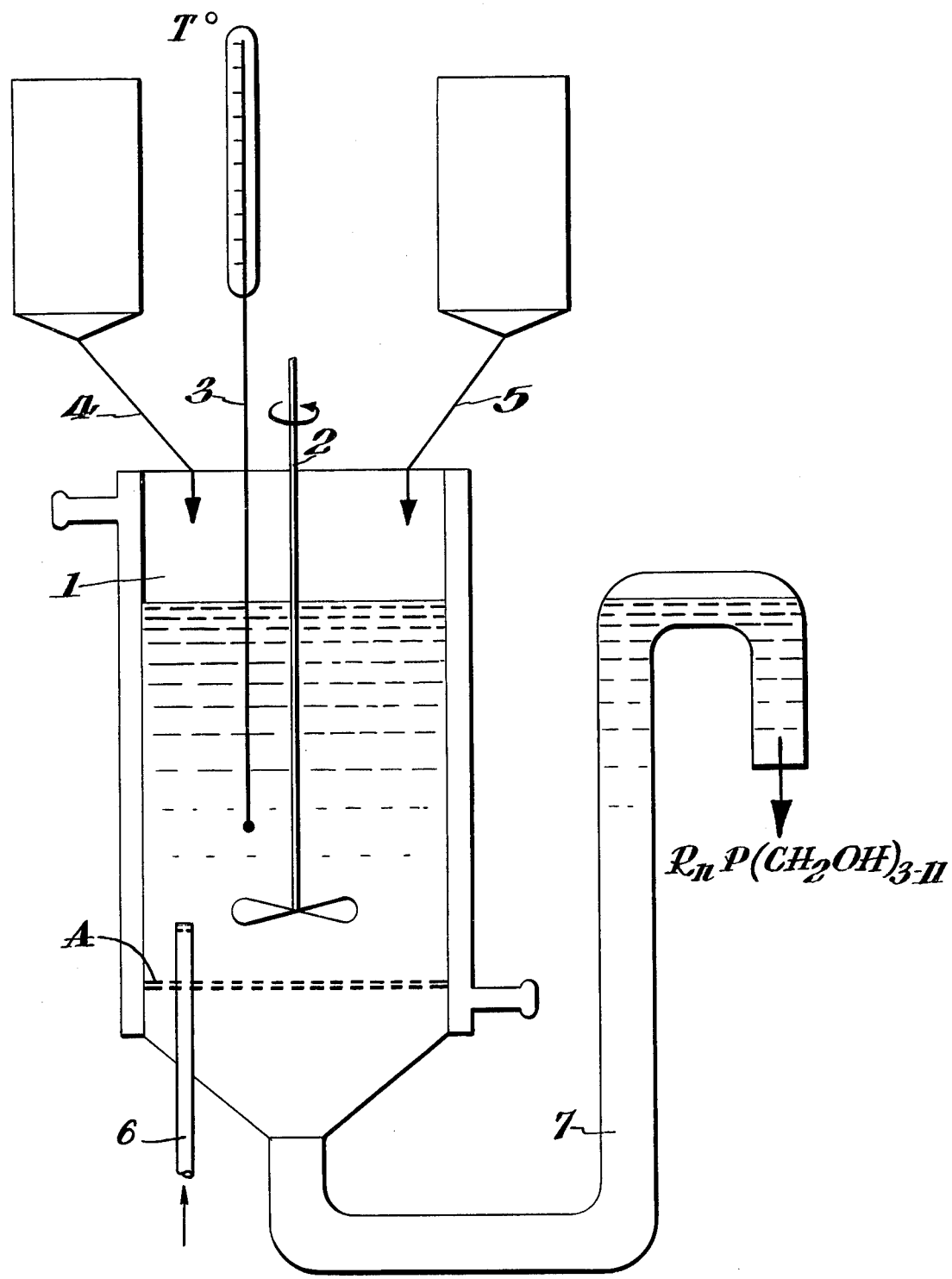

PRODUCTION OF (HYDROXYMETHYL)-ALKYL, CYCLOALKYL AND ARALKYLPHOSPHINES

The present invention relates to a process for making (hydroxymethyl)-alkyl, cycloalkyl or aralkyl-phosphines of the general formula:

$$R_nP(CH_2OH)_{3-n}$$

in which n stands for 1 or 2 and R stands for identical or different, substituted or unsubstituted alkyl, cycloalkyl or aralkyl radicals containing from 1 to 18, preferably from 1 to 4, more preferably from 1 to 2 carbon atoms.

It has already been described that (hydroxymethyl)-alkyl phosphines can be made by reacting primary and secondary phosphines with paraformaldehyde under pressure in an autoclave at temperatures within the range 60° and 90° C (cf.E.I. Grinstein, A. B. Bruker and L. Z. Soborovskii, Doklady Adk. USSR Pat. No. 139, 1359 (1961); USSR Pat. No. 138 (1960) and Zh.Obshch.-Khim 36 (2) 302, 1966).

This process presents a series of adverse effects. If carried out at elevated temperature under pressure, the Buckler-Tripett rearrangement reaction is found to occur to an increasing extent with the resultant formation of isomeric alkyl phosphine oxides, which cannot be separated completely during the work-up of the reaction product by distillation under vacuum (cf. H. Hellmann, J. Bader, H. Birkner and O. Schumacher, Lieb. Ann. 659 (1962) and S. A. Buckler, J.Amer.-Chem.Soc. 82, 4215 (1960). It is also substantially impossible for that pressure reaction to be carried out under commercially attractive conditions as the alkyl phosphines, which are used therein, combine in themselves an extreme toxicity with flammability in contact with air. In other words, it is necessary for them to be used in relatively small batches to ensure safe operation, which in turn means limited space/time-yields.

A further process for making hydroxymethyl phosphines has been described in U.S. Pat. No. 3,660,495, wherein an aqueous formaldehyde solution is reacted with hydrogen phosphide. To obtain high yields, it is, however, necessary for that process to be carried out in contact with a tetrakis-(hydroxymethyl)-phosphonium chloride catalyst under pressure, naturally with the adverse effects referred to hereinabove.

A further disadvantage encountered upon the use of an aqueous formaldehyde solution resides in the formation of the respective hydroxymethylphosphine oxide. As taught in German patent specification "Offenlegungsschrift" No. 1,930,521, this compound is produced primarily under pressure by reaction with water in the presence of a formaldehyde catalyst.

In accordance with the present invention, we have now unexpectedly found that the above (hydroxymethyl)-alkyl, cycloalkyl or aralkyl phosphines can be made continuously or discontinuously, rapidly and safely, at atmospheric pressure, in quantitative yields and substantially free from by-products by a process comprising: reacting the corresponding mono- or di-, alkyl, cycloalkyl or aralkylphosphines at atmospheric pressure and at temperatures lower than 40° C with formaldehyde, paraformaldehyde or trioxane in the presence of polar solvents being inert with respect to the resulting reaction product; and separating the solvent from the reaction product.

The reaction should more preferably be effected with the use of such inert solvents as boil at temperatures lower than 120° C.

The solvents which should conveniently be used include alcohols, glycols, ethers, alkylated formamides, aliphatic or aromatic nitriles, halogenated aliphatic or aromatic hydrocarbons, cyclic and linear sulfones, carboxylic anhydrides or esters, N-alkylated carboxylic acid amides, such as methanol, ethanol, propanol, isopropanol, chloroform, methylene chloride, methyl or ethyl acetate, or mixtures thereof.

It has also been found that it is possible for the reaction periods to be shortened considerably by effecting the reaction in the presence of a catalyst, which should preferably be used in proportions within the range 100 ppm and 0.1%, based on the quantity of formaldehyde used.

The catalysts which should preferably be used include metal salts belonging to group II or VIII of the Periodic System of the elements as well as phosphates, phosphites, hypophosphites or phosphonium compounds of the formula $(R_2R'_2P)X$ or $(RR'_3P)X$, in which R and R', respectively, stands for substituted or unsubstituted organic radicals and X stands for chlorine, $Br^-$, $I^-$, $CH_3COO^-$ or $H_2PO_4^-$.

The metal salts which should more preferably be used are selected from those of platinum, rhodium, cadmium or nickel, if desired in complex form, the chlorides being preferred.

The reaction should conveniently be carried out under a protective gas, which should be selected from nitrogen, argon or carbon dioxide.

In those cases in which the present process is carried out continuously, it is most advantageous for it to be effected in a reactor which is subdivided into two reactor portions by means of a partition wall permeable to liquid matter, e.g., a filter plate, a frit or a diaphragm, and which is initially fed with a solution of the (hydroxymethyl)-phosphine to be made, in an organic solvent.

The first reactor portion having the above solution therein is fed with paraformaldehyde, which is suspended therein. The resulting suspension is stirred intensely and admixed simultaneously with the respective mono- or di- alkyl, cycloalkyl or aralkyl phosphine, paraformaldehyde and solvent, which are supplied continuously in proportions corresponding to the quantity of newly formed (hydroxymethyl)-phosphine solution, and the latter is continuously removed from the second reactor portion. The solution is freed from the solvent which is recycled to the first reactor portion. It is good practice for that reaction to be carried out at temperatures within the range 30° and 35° C.

Depending on the particular reaction conditions selected, the process of the present invention yields up to 80% solutions of (hydroxymethyl)-alkyl, cycloalkyl or aralkylphosphines which are easy to obtain in the form of 100% material by removing the solvent used in each particular case, under vacuum.

By the use of a catalyst, it is possible for the reaction periods to be shortened by up to 30%.

It is good practice for discontinuous operation to prepare a solution of paraformaldehyde or formaldehyde or trioxane in the organic solvent and to introduce the starting phosphine thereinto, preferably under a protective gas with thorough agitation at temperatures within the range 30° and 35° C. Liquid phosphines should be added dropwise in dilute or undilute form, or in admixture with a stream of inert gas, if they are sufficiently volatile. The reaction heat set free is dissipated by cooling from the outside. The reaction which may be carried out in the presence of a catalyst, if desired, is terminated as soon as the aldehyde is found to have been consumed quantitatively. The reaction product is a clear solution from which the particular (hydroxymethyl)-alkyl, cycloalkyl or aralkylphosphine is obtained in quantitative yields, after removal of the solvent under vacuum.

The process of the present invention compares very favorably with prior art methods in the following aspects: It is easy to carry out and substantially safe in operation and combines this with high yields and substantially quantitative conversion rates. it also produces very pure and homogeneous reaction products and it is possible for it to be carried out in continuous fashion.

The phosphines made by the present process are valuable reactive intermediates which find widespread uses, especially in the synthetic production of flameproofing agents, pharmaceutical preparations and textile aids. They have also gained interest for use as activators in the production of flameproof polyurethanes.

The following Examples illustrate the invention.

EXAMPLE 1

(Discontinuous operation)

240 g (8 mols) of paraformaldehyde was suspended under nitrogen in 287 g of methanol in a reactor having a capacity of 1 liter. The reactor was provided with an intense agitator, thermometer, gas inlet and gas outlet, reflux condenser and cooling coil, and series-connected to a cooling trap maintained at $-78°$ C. For reasons of safety, the whole apparatus was connected to an off-gas incinerator system.

194 g of methylphosphine was introduced into the suspension with vigorous agitation. The temperature was maintained at 30° C by cooling. After 4 hours, a clear 60% methanolic solution of bis-(hydroxymethyl)-methylphosphine was obtained, from which the pure phosphine was easy to separate by removing the solvent under vacuum at temperatures of up to 30° C. The solvent was recovered quantitatively and used again. 431 g of 100 % bis-(hydroxymethyl)-methylphosphine was obtained in the form of a colorless liquid distillable under vacuum. $Bp_{3mm\ Hg}$ 89°–90° C; $n_D^{20}$ = 1.5328.

The bis-(hydroxymethyl)-methylphosphine so made was found to be identical in its IR- and NMR-spectrums with a comparative product made by the pressure reaction described by E. I. Grinstein.

The cooling trap placed downstream of the reactor contained 2 g of unreacted methylphosphine which could be used again. The conversion rate, based on methylphosphine, was 99%.

Content (iodometric titration in acid medium) 100%
Analysis: $C_3H_9O_2P$
Calculated: C 33.3%, H 8.3%, P 28.7%;
Found: C 33.5%, H 8.5%, P 28.4%.

The experiment was repeated save that the methanol was replaced once by ethanol and once by methylene chloride. Similar results were obtained. The same product was also obtained in those cases in which the paraformaldehyde was replaced once by formaldehyde (40% methanolic solution) and once by trioxane.

EXAMPLE 2

The procedure was the same as that described in Example 1 save that anhydrous cadmium chloride (0.01%) was added as a catalyst to the reaction mixture. The reaction period was thereby shortened to 3 hours, or reduced by 25%. The bis-(hydroxymethyl)-methylphosphine so made corresponded to the product obtained in Example 1. The yield was substantially 100%. The product was free from contaminants.

In the following table there are specified further catalysts for use in the process of the present invention, the reaction periods necessary in each particular case, and the % reductions of the reaction periods, based on the standard reaction period of Example 1.

Table

| Catalyst | Catalyst quantity in ppm | Reaction period in hours | % Reduction of reaction period |
|---|---|---|---|
| None Example 1 | — | 4.8 | — |
| $PtCl_2$ | 1000 | 2.8 | 30.0 |
| $K_2PtCl_6$ | 100 | 2.8 | 30.0 |
| $NiCl_2$ | 500 | 3.6 | 10.0 |
| $[(CH_3)P(CH_2OH)_3]Cl$ | 1000 | 3.0 | 25.0 |
| $[(CH_3)P(CH_2OH)_2]Cl$ | 500 | 3.5 | 12.5 |
| $[(CH_3)P(CH_2OH)_3]Cl$ | 100 | 3.8 | 5.0 |
| $NaH_2PO_2$ | 1000 | 3.8 | 5.0 |
| $Na(PH_3)_2(CO)_4$ | 500 | 3.0 | 25 |
| $Cr(PH_3)_2(CO)_4$ | 500 | 3.0 | 25 |

EXAMPLE 3

The procedure was the same as that described in Example 1, but 126 g of dimethylphosphine was reacted with 60 g of paraformaldehyde for 3 hours at 20°–25° C. The methanol was removed under vacuum and 180 g (97.8% yield) of (hydroxymethyl)-dimethylphosphine was obtained. The dimethylphosphine conversion rate was 97.5%.

Content: (iodometric titration in acid medium) 99%
Analysis: $C_3H_9OP$
Calculated: C 39.1%, H 9.9%, P 33.7%;
Found: C 39.4%, H 10.2%, P 33.4%.

The (hydroxymethyl)-dimethylphosphine so made was a colorless liquid distillable under vacuum. $Bp_{10\ mm\ Hg}$ 50°–51° C; $n_D$ 1.5016. In its chemical and physical properties, the product was identical with a comparative product made by the autoclave process described by E. I. Grinstein.

It was possible for the reaction period to be shortened up to about 30%, depending on the particular catalyst and catalyst quantity used.

EXAMPLE 4

The procedure was the same as that described in Example 1, but 64 g of ethylphosphine was reacted with 60 g of paraformaldehyde for 3 hours at 30°–35° C. After removal of the methanol under vacuum, there was obtained 122 g (100% yield, based on paraformaldehyde) of bis-(hydroxy-methyl)-ethylphosphine. The diethylphosphine conversion rate was 96.8%.

Content: (iodometric titration in acid medium) 99%
Analysis: $C_4H_{11}O_2P$
Calculated: C 39.3%, H 9.0%, P 25.4%;
Found: C 39.6%, H 9.2%, P 25.5%.

The bis-(hydroxymethyl)-ethylphosphine so made was a colorless liquid distillable under vacuum. $Bp_{1mm\ Hg}$ 81°–83° C; $n_D$ 1.5253. The compound was identical with a comparative product made by the autoclave process described by E. I. Grinstein.

EXAMPLE 5

(Continuous operation)

The one FIGURE of the drawing schematically illustrates a device wherein a suspension of paraformaldehyde in methanol was introduced into a coolable double-walled reactor 1 about 80 cm long and 8 cm wide provided with an efficient agitator 2 and tubular means receiving a thermometer 3. The reactor 1 was furthermore provided, near its lower end (about 3 cm above its bottom portion), with a filter plate A and, near its upper end, with two dosing means supplying methanol via conduit 4 and paraformaldehyde via conduit 5, respectively. By means of a tubular gas inlet projecting into the reactor from below, 22.4 l/h of methylphosphine (1 mol/h) was introduced continuously via conduit 6, countercurrently with respect to the suspension, under inert gas with thorough agitation, and jointly with 60 g/h of paraformaldehyde (2 mols/h). At the same time, 200 g/h of the resulting clear solution of bis-(hydroxymethyl)-methylphosphine in methanol was removed continuously via conduit 7, below the filter plate A. In a distillation stage downstream of the reactor, the solution was freed continuously from the solvent under vacuum and the solvent was recycled to the reactor so as to have constant stoichiometric conditions therein (about 92 g/h of methanol).

The reaction was effected with exclusion of oxygen at a temperature lower than 40° C.

Bis-(hydroxymethyl)-methylphosphine was obtained substantially in a 100% yield. The product was identical with that described in Example 1 and could not be found to contain bis-(hydroxymethyl)-methylphosphine oxide.

In the above continuous operation, it was possible for the methylphosphine to be successfully replaced by dimethylphosphine or ethylphosphine, and for the methanol to be replaced by ethanol or methylene chloride. To accelerate the reaction, it was possible for it to be carried out in the presence of the above catalysts, which enabled the space/time yields to be improved by up to 20%.

In this Example it was also possible for the reaction period to be shortened considerably by the use of the above catalyst.

We claim:
1. In the process for making (hydroxymethyl)-alkylphosphines of the formula:

$$R_nP(CH_2OH)_{3-n}$$

in which $n$ is 1 or 2 and R is alkyl having from 1 to 4 carbon atoms, by reacting the corresponding mono- or di-alkylphosphines at atmospheric pressure with paraformaldehyde in the presence of a polar organic solvent being inert with respect to the resulting reaction product, and separating the solvent from the solution of the reaction product, the improvement which comprises producing the said (hydroxymethyl)-alkylphosphines continuously by introducing initially a starting solution of (hydroxymethyl)-alkylphosphine in the organic solvent into a reactor being subdivided into two reactor portions by means of a partition wall being permeable to the solution of the reaction product and being impermeable to the paraformaldehyde suspended in the said starting solution in the first reactor portion; intensively stirring and simultaneously admixing the paraformaldehyde suspension obtained with the respective mono- or di-alkylphosphine, paraformaldehyde and solvent, which are supplied continuously and in proportions corresponding to the quantity of (hydroxymethyl)-alkylphosphine solutions newly formed at temperatures lower than 40° C; removing those solutions continuously from the second portion of the reactor; separating the solvent therefrom and recycling it to the first reactor portion.

2. The process as claimed in claim 1, wherein the reaction is effected in the additional presence of a catalyst.

3. The process as claimed in claim 2, wherein the catalyst is used in proportions within the range 100 ppm and 0.1 weight %, based on the weight of formaldehyde.

4. The process as claimed in claim 2, wherein the catalysts used are selected from salts of metals belonging to group II or VIII of the Periodic System of the elements, phosphates, phosphites, hypophosphites or phosphonium compounds of the formula $(R_2R'_2P)X$ or $(RR'_3P)X$, wherein R is methyl, R' is hydroxymethyl and X is $Cl^-$, $Br^-$, $I^-$, $CH_3COO^-$ or $H_2PO_4^-$.

* * * * *